United States Patent [19]

Forbes et al.

[11] Patent Number: 5,687,735
[45] Date of Patent: Nov. 18, 1997

[54] ROBUST TIME-DIVERSITY FILTER AND METHOD FOR REMOVING ELECTROMAGNETIC INTERFERENCE

[75] Inventors: Alfred Dean Forbes, Palo Alto; Eric D. Helfenbein, Sunnyvale, both of Calif.

[73] Assignee: Hewlett-Packard Company, Palo Alto, Calif.

[21] Appl. No.: 624,194

[22] Filed: Mar. 28, 1996

[51] Int. Cl.$^6$ .............................. A61B 5/402; G06F 15/20
[52] U.S. Cl. ............................ 128/696; 128/901; 364/574
[58] Field of Search .............................. 128/696, 901; 364/724.01, 572, 573, 574

[56] References Cited

U.S. PATENT DOCUMENTS

| 4,422,459 | 12/1983 | Simson | 128/702 |
| 5,278,777 | 1/1994 | Cummins | 364/574 |

FOREIGN PATENT DOCUMENTS 0 588 526 A1  8/1993  European Pat. Off. .

OTHER PUBLICATIONS

Widrow, Bernard et al., "Adaptive Noise Cancelling: Principles and Applications", *Proceeding of theIEEE*, vol. 63, No. 12, Dec. 1975, pp. 1692–1716.

Widrow, Bernard et al., "Adaptive Signal Processing", *Library of Congress Cataloging in Publication Data*, Prentice–Hall, Inc., Englewood Cliffs, N.J. 07632, 1985, pp. vii–341.

Haykin, Simon, "Adaptive Filter Theory", *Library of Congress Cataloging in Publication Data*, Prentice–Hall, Inc., Englewood Cliffs, N.J. 07632, 1985, pp. vii–315.

Bloomfield, Peter et al., "Least Absolute Deviations", *Theory, Applications and Algorithms*, Birkhauser, Boston, Basel, Stuttgart, 1983 (Progress in probability and statistics; vol. 6), pp. xiii–1.

Rousseeuw, Peter et al., "Robust Regression and Outlier Detection", *Library of Congress Cataloging in Publication Data*, John Wiley & Sons, Inc., 1987, pp. xiii–19.

*Primary Examiner*—Scott M. Getzow

[57] ABSTRACT

An apparatus and method for the filtering of signals collected during a period that includes a quiet ("signal-free") epoch and an event epoch is disclosed. The apparatus includes a means for generating electrical digitized signals of the event episode, memory for receiving and storing the digitized signals of the event episode, an event detector for determining the event epoch and the quiet epoch of the event episode in the digitized signals, a spectrum analyzer to analyze the power spectrum of the digitized signals of at least one event episode, an estimator to estimate electromagnetic interference (EMI) based on the digitized signals of the quiet epoch and the frequencies obtained in the spectral analysis; and a subtractor to subtract the estimated EMI from the digitized signals of the event epoch. The resulting signals are signals of the event epoch with reduced EMI. The apparatus uses basis function(s) at one or more dominant frequencies determined from the spectral analysis to curve-fit data of the quiet-epoch signals to generate the EMI estimate.

25 Claims, 8 Drawing Sheets

ROBUST TIME-DIVERSITY FILTER AND METHOD FOR REMOVING ELECTROMAGNETIC INTERFERENCE

FIELD OF THE INVENTION

The present invention is related to filtering of signals, and more particularly, related to removing electromagnetic interference from signals of event episodes each of which has an event epoch (that has meaningful signals) and a quiet (signal-free) epoch.

BACKGROUND

Digital recordings of signals from an object (e.g., physiological signals such as ECG from a patient often contain unwanted electromagnetic interference (EMI). It is desirable to remove the EMI through a filtering technique so that the underlying signal (e.g., physiological signal) can be extracted and subsequently processed for its intended purpose.

The dominant EMI in signals is usually a result of the sinusoidal power line ("mains"). Thus, most of the EMI appears in the recorded waveforms as sinusoids at the power line frequency and a few of its harmnonics. A typical method for removal of power line interference is to process the waveform with a digital notch (stopband) filter with its notch at the line frequency. Since harmonics of the power line frequency will not be canceled by a fixed notch, a "comb" filter is often used, employing a series of notch filters at the different frequencies. However, both digital and analog implementations of notch and comb filters have a number of disadvantages. First, notch filters "ring," thereby causing unwanted signal distortions which are due solely to the filtering process itself. In addition, as the notch is made narrower, the tendency to ring increases. Comb filters multiply the ringing effects of notch filters.

Another disadvantage of notch filters is that they also remove any portion of the signal of interest that has the same frequency as the notch (when there is an overlap of frequency content between the underlying signal of interest and the EMI). Yet another disadvantage of notch or comb filters is that they are not adaptive for changes in interference. Power line interference often varies around the nominal frequency. Because fixed frequency notch filters do not adapt to changing EMI frequencies, a wider notch is needed. A wider notch, however, increases signal distortion.

Adaptive filtering methods (Widrow et at., "Adaptive Noise Canceling: Principles and Applications," Proc IEEE, Vol. 63, No. 12, pp. 1692–1716, 1975; Widrow et at., *Adaptive Signal Processing*, New Jersey, Prentice-Hall, 1985; Haykin, S., *Adaptive Filter Theory*, 2nd ed., New Jersey, Prentice-Hall, 1991) have been developed to remove additive noise or interference from various types of signals. These methods are designed to adapt to changing interference frequencies. Although adequate in many applications, such adaptive filtering methods also have disadvantages. Adaptive noise filters usually rely on "spatial diversity," i.e., they require a signal-independent noise/interference "sensor" to produce a reference input. This reference input must contain only the interference, which must be correlated with the interference present in the primary input. In many applications it may not be possible to 1) produce the required reference input, 2) ensure that the reference input will be correlated to the primary noise, or 3) ensure that the reference input does not contain a significant amount of the primary signal ("crosstalk"). Furthermore, if the interference has a large amount of short-term variation in amplitude or frequency, the convergence of the adaptive filter may be too slow to track the interference. As a result, the filter will perform poorly and may actually introduce interference. Additionally, such adaptive filters may not be able to cope with interference comprised of multiple frequencies. In many cases, they cannot easily be modified to do so.

SUMMARY

The present invention provides EMI filtering of signals of an event episode that includes an event epoch (which has signals of interest) and a quiet (i.e., free of meaningful signal, also called "signal-free" herein) epoch, overcoming the disadvantages of the aforementioned prior art methods. An apparatus provided by the present invention for such filtering includes a means for generating electrical digitized signals of the event episode, memory for receiving and storing the digitized signals of the event episode, an event detector for determining the event epoch and the quiet epoch of the event episode in the digitized signals, a spectrum analyzer to analyze the power spectrum of the digitized signals of at least one event episode, an estimator to estimate electromagnetic interference (EMI) based on the digitized signals (i.e., input) of a quiet epoch and the frequencies obtained in the spectral analysis, and a subtractor for subtracting the estimated EMI from the digitized signals of the event epoch, such that the resulting signals are signals of the event epoch with reduced EMI.

To estimate the EMI at the event epoch, the EMI at the quiet epoch adjacent to the event epoch is estimated first and extended to span the event epoch. The apparatus uses basis function(s) (preferably combining a sine wave and a cosine wave of an EMI frequency in the case of sinusoidal EMI) at one or more frequencies determined from the spectral analysis to curve-fit (or approximate) data of the signals of the quiet epoch to generate the EMI estimate. To curve-fit line frequency EMI, preferably, only one sine wave and only one cosine wave at each EMI frequency are combined to curve-fit the data of the quiet epoch. The amplitude of the sine wave and the amplitude of the cosine wave are adjusted to curve-fit the interferences of the quiet epoch and therefore are not necessarily the same.

Harmonics at higher frequencies for line EMI can be similarly estimated. An embodiment of the "basis function filter" filtering method according to the present invention— the "sinusoidal trend filter" (STF)—can be used to remove line frequency EMI, as well as its harmonics (i.e., harmonic frequencies, herein referring to those that are higher than the fundamental frequency) from high resolution digital recordings. As used herein, the term "remove" means partially or substantially remove.

The filter and method of the present invention have advantages over current filters and filtering methods for EMI removal. For example, the sinusoidal trend filter removes line frequency EMI and its harmonics without causing ringing. The filter can be used to remove the EMI while leaving the signal energy of the event of interest at EMI frequencies intact. Since EMI often appears as short-term stationary waveforms (e.g., sinusoids), if event signals contain energy at the same frequencies as the EMI, the two can be separated.

Figure 1:
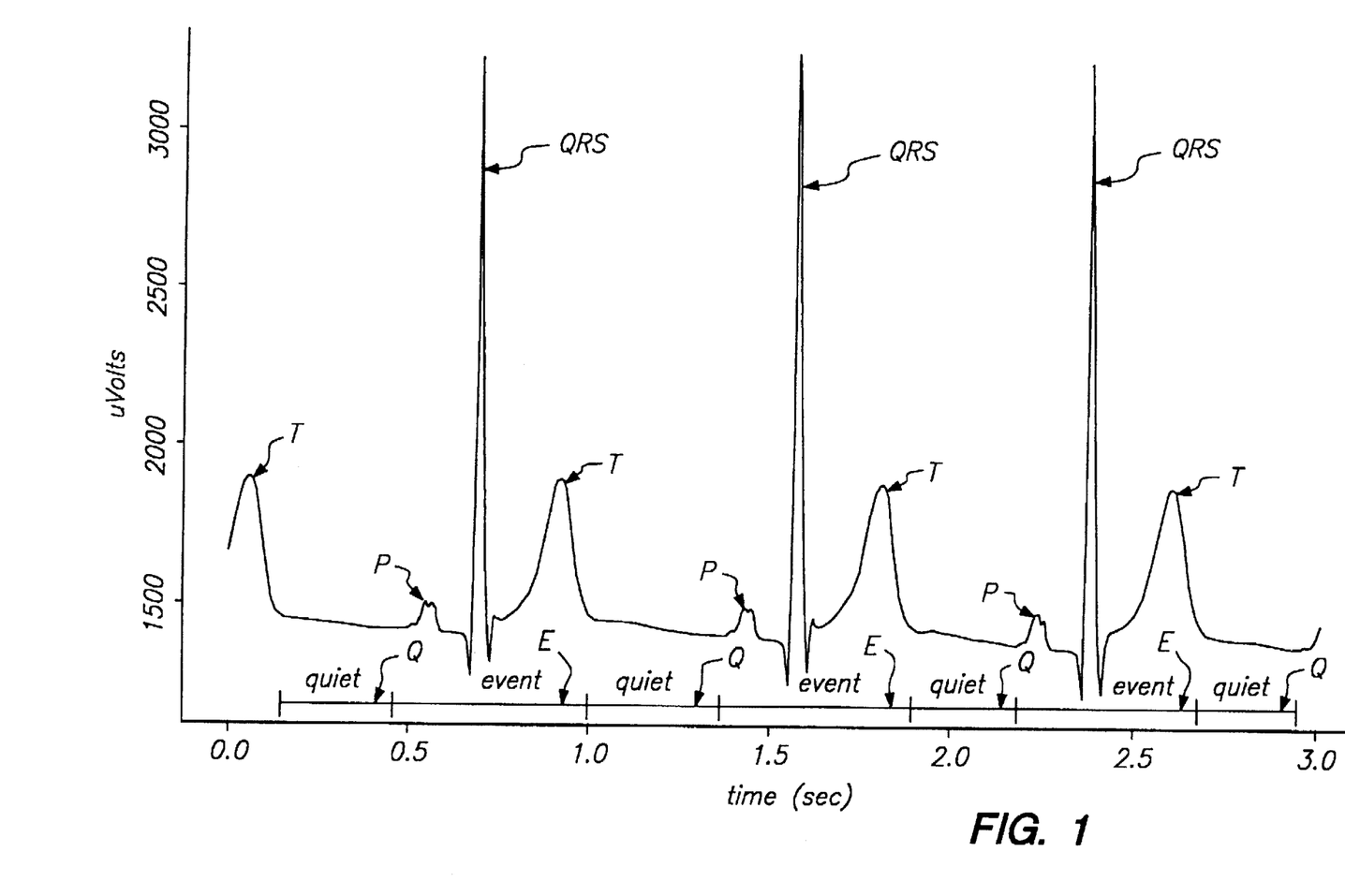
FIG. 1 shows a typical ECG tracing having quiet epochs and event epochs.

Because the filtering is performed in the time domain, robust methods such as least one-norm and least-trimmed-squares can be used. Use of these methods makes the method less sensitive to outliers in the waveform (e.g., impulsive noise spikes) which can cause typical methods to distort the signal (e.g., a noise spike during a quiet epoch may cause a notch filter to ring during the succeeding event epoch). Since the EMI is estimated over short quiet epochs, the basis function filter (e.g., STF) can rapidly adapt to phase and amplitude jumps in the interference. As an illustration, the STF filter has been successfully used to the remove 60 Hz line frequency EMI and its dominant 180 Hz and 300 Hz harmonics from high resolution electro-cardiogram (ECG) recordings. STF-filtered heartbeat "episodes" (i.e., time intervals) having quiet epochs and event epochs are shown in FIG. 1. The general basis function filter can be applied to remove short-term stationary EMI (sinusoidal or nonsinusoidal) at various frequencies from physiological or non-physiological signals of an event episode that contains an event epoch and a quiet epoch.

BRIEF DESCRIPTION OF THE DRAWINGS

The following figures, which show the embodiments of the present invention, are included to better illustrate the apparatus and method of the present invention. In these figures, like numerals represent like features in the several views.

DETAILED DESCRIPTION OF THE INVENTION

The present invention provides a "basis function filter" that matches EMI signals during a quiet epoch with basis functions of one or more frequencies identified by spectral analysis of signals collected during a period including at least a portion of the quiet epoch. FIG. 1 shows an example of signals (ECG) that have been filtered by the basis function filter (the STF for line EMI) of the present invention. It is understood that ECG is given for illustration purposes and other types of signals can be filtered using the method and apparatus of the present invention. In this example, each heart beat (the time interval of which is referred to as an event episode) has a P wave marked by P, a QRS complex marked by QRS, and a T wave marked by T. The interval Q between the tail end of the T wave of the preceding heart beat and the beginning of the P wave of a heartbeat is considered to contain no significant "event information," i.e., information that represents the activity of the heart. This interval is referred to as the "quiet epoch" herein since it is "signal-free" and contains essentially only electromagnetic interference. The rest of the interval (of the heartbeat) is referred to as the "event epoch," E, which corresponds to the PQRST waves.

Preferred Embodiment of the Filter

Figure 2:
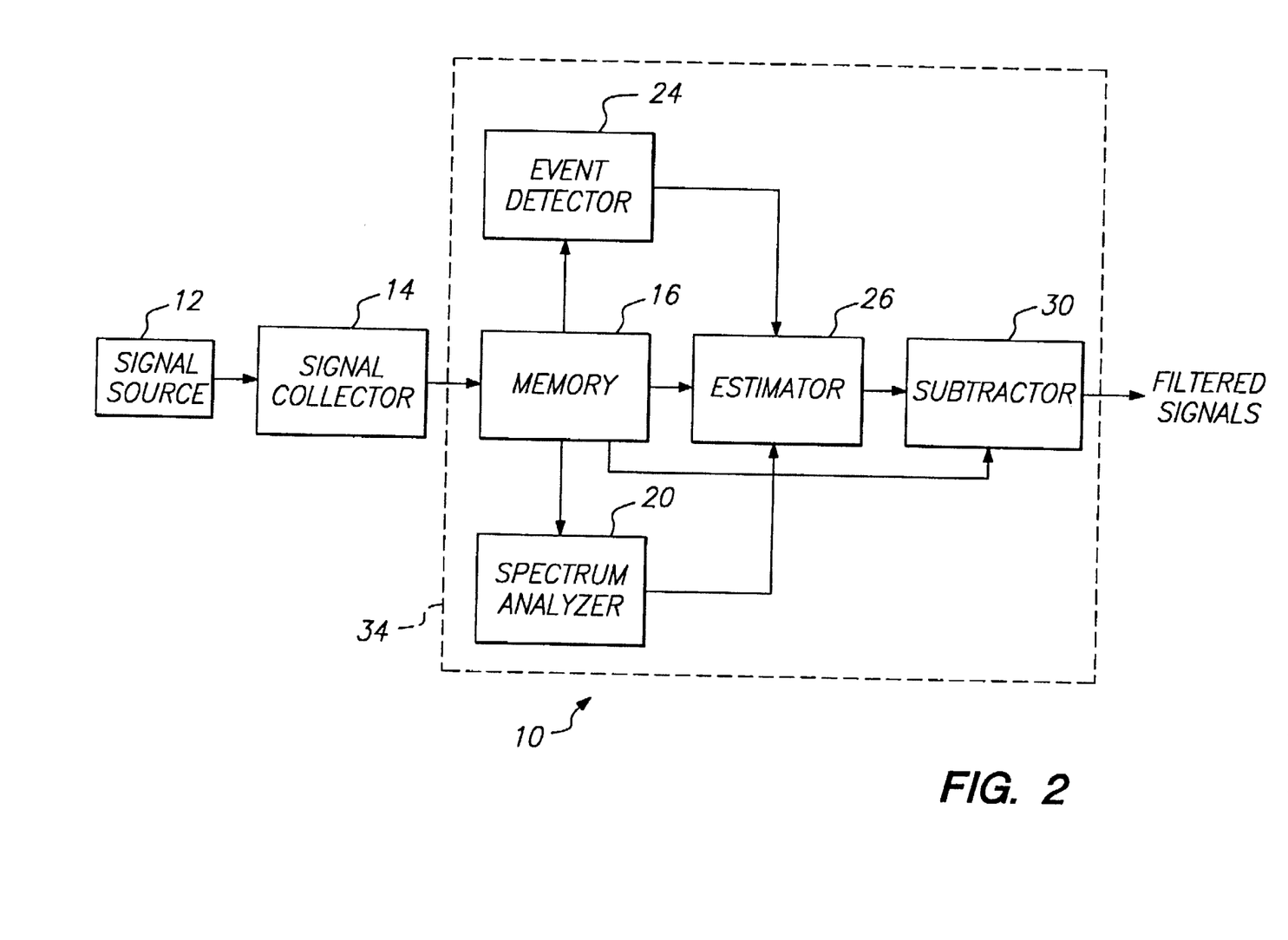
FIG. 2 shows a schematic representation of the filter of the present invention.

FIG. 2 schematically shows an embodiment of the basis function filter 10 of the present invention. Signals generated by a signal source 12 (e.g., a patient) are collected by a device 14 that converts the signals into a form receivable and storable by a memory 16. The device 14 can include sensor(s) (e.g. ECG electrodes) that collect electrical signals (i.e., input) from the signal source 12. It can also contain devices that convert other signals (e.g., transducers, photodetectors, and the like, that convert vibration, sound, light, etc.) into electrical signals. The device 14 can also contain an amplifier to amplify the signals from the sensors and can include an analog to digital (A/D) converter to convert analog signals into digital signals.

Digitized signals from the memory 16 are analyzed by a spectrum analyzer 20 to obtain information on the more dominant frequencies of the EMI in the signals. The digitized signals from the memory 16 are also analyzed by an event detector 24 to determine the beginning and the end of each quiet epoch and of each event epoch. The information about the dominant frequencies and the beginnings and ends of event and quiet epochs are transmitted to an estimator 26 to estimate the EMI of the event epochs.

The estimator 26, based on the dominant frequencies obtained in the spectral analysis, can be used to generate basis functions that match the amplitude and phase of the collected signals (stored as digitized signals in the memory 16) of a quiet epoch of interest. These basis functions are weighted to become the EMI estimate of that quiet epoch. These basis functions are extended to span the event epoch adjacent (e.g., following) that quiet epoch, thereby resulting in the EMI estimate of that event epoch.

A subtractor 30 is used to subtract the EMI estimate from the collected signals to result in filtered signals that have reduced EMI. The EMI estimate of an event epoch is subtracted from the corresponding collected signals of that event epoch. If desired, the EMI estimate of a quiet epoch can be subtracted from the corresponding collected signals during that quiet epoch. In this way, filtered signals of an event episode (e.g., of heartbeat), or for a series of event episodes (e.g. a few minutes of ECG signals corresponding to heartbeats) can be obtained.

Preferably, once digitized signals are obtained (e.g., from an A/D converter), the signal is processed by an electronic computer 34 to result in the filtered signals. In this case, the memory, spectrum analyzer, estimator, and subtractor are all part of the electronic computer. However, it is understood that individual electronic devices or circuits can be used to perform the functions of the memory, spectrum analyzer, estimator, the subtractor, or a combination thereof.

Figure 3:
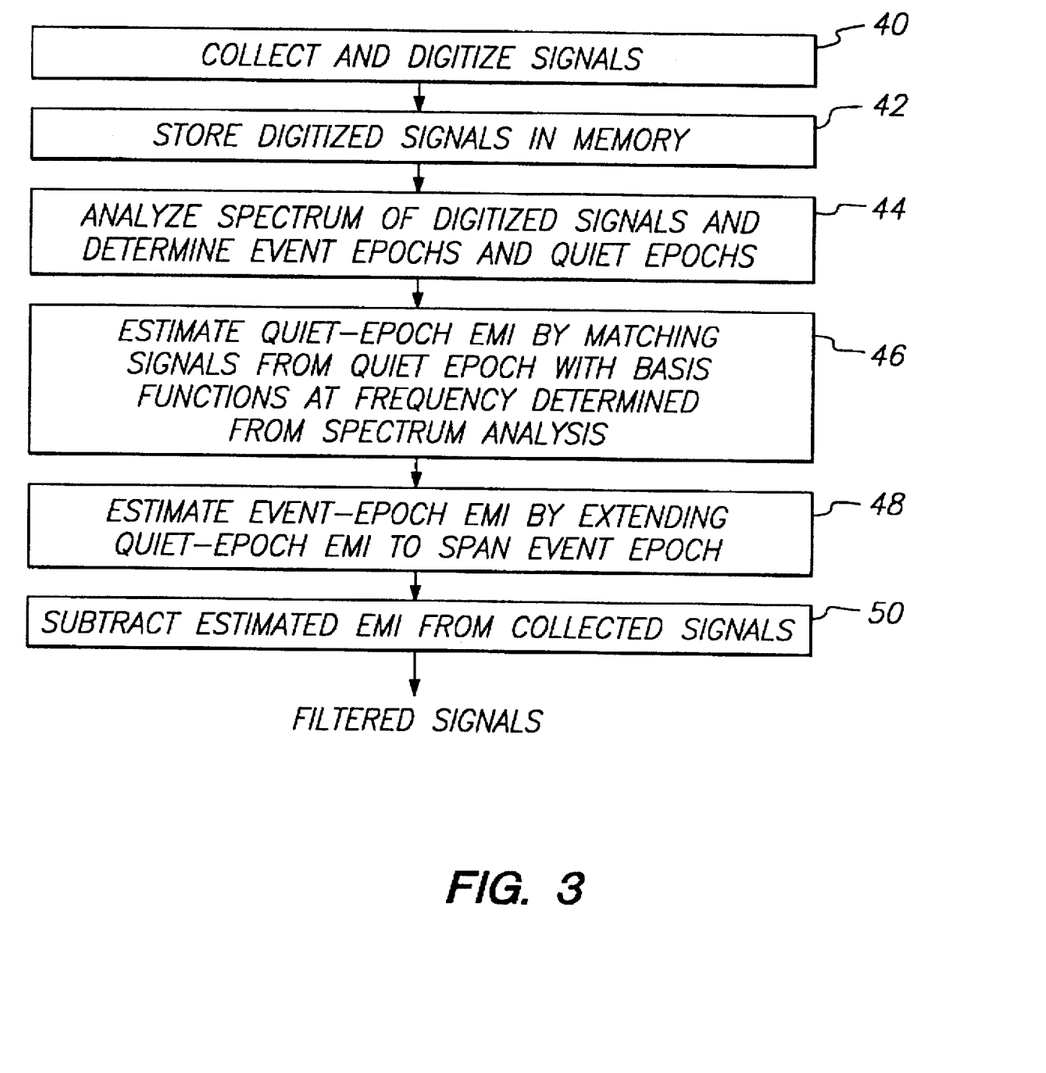
FIG. 3 shows a flow-chart illustrating the method of filtering EMI according to the present invention.

FIG. 3 shows the filtering method according to the present invention. First, digitized signals corresponding to the events of interests are obtained (block 40). This can be done by collecting electrical signals (i.e., input) from a signal source or converting nonelectrical signals (e.g., ultrasound) to electrical signals and then digitizing the electrical signals. The digitized signals are stored in a memory (block 42).

The digitized signals are then spectrally analyzed to obtain the dominant EMI frequencies. In addition, the signals are analyzed to determine the quiet epochs and event epochs of each event epoch (block 44). Although it is preferable that the digitized signals from the memory are analyzed electronically by computer algorithms for this event analysis, it is contemplated that such an analysis might be done analogy, or even manually by a person.

The EMI estimates of the quiet epoch(s) are obtained based on the dominant EMI frequencies and by matching basis functions at these frequencies (which can be one or more frequencies) to the collected signals of the quiet epochs (block 46). The EMI estimate of the event epoch is obtained by extending the basis functions from the quiet epoch to the adjacent event epoch (block 48). Finally, filtered signals are obtained by subtracting the EMI estimate (s) from the corresponding collected signals.

The Basis Function Filter

The basis function filter can be applied to waveforms having "time diversity" of the signal and noise. Having "time diversity" means that the signals (i.e., input) over time can be divided into discrete periods of signal and noise (i.e., signal-free). The "signal-free" periods are "quiet epochs" during which the signal of interest (i.e., meaningful signal) is absent (or essentially absent or can be made to appear so, e.g., by filtering out signal of interest from such quiet epoch), yet the interference is present. These epochs are referred to as "quiet epochs" since they are quiet in terms of signal content of the event of interest. These quiet epochs surround epochs where the signals of interest are present, albeit corrupted with the unwanted interference. These epochs are referred to as "event epochs," since they will contain signals of the events of interest. The ECG is an example of such a signal. The electrical activity associated with each heartbeat (the "event" to be examined) is usually surrounded by brief periods lacking cardiac electrical activity in which only the interference is present (i.e., the "quiet epochs"), as shown in FIG. 1. Another example is the sound emitted by a pump driving a pulsatile flow. The basis function filter can be adapted for a variety of signals. For illustration, application for filtration of ECG signals to remove line EMI is described in the following. A person skilled in the art will be able to modify a filter for other applications based on the present disclosure.

The EMI frequency (or frequencies) is first measured from a power spectrum of the waveform (i.e., data of signals collected). For example, although the line frequency is about 60 Hz, since the power line frequency often varies by as much as 0.1%, the frequency of the power line and its harmonics are spectrally analyzed. Basis functions (e.g., sinusoids in the case of line EMI) at these measured frequencies are fitted to a quiet epoch to produce a regressive estimate of the EMI. This EMI estimate is referred to as the "sinusoidal trend" for sinusoidal EMI. The basis functions may be more complex for other EMI waveforms, e.g. square wave, etc. However, the basis functions of many sorts of EMI with regular waveforms can be determined by one skilled in the art (e.g., square waves can be represented by a combination of sinusoids). The EMI is assumed to be locally stationary (i.e., it does not vary significantly during the period of an event), and can thus be represented as a linear combination of basis functions (e.g., a few sinusoids for line EMI). This interference estimate is then extended from the quiet epoch across the adjacent event epoch and is subtracted from the collected signal there, thereby leaving the underlying signal essentially free of EMI. Because of the locally stationary characteristics of EMI with time, it is to be understood that although preferably signals collected over a period of time that includes the event episode of interest (which is, for example, the period of one heart beat) be spectrally analyzed to determine the EMI frequency, a period that includes only a portion, or even none of the event episode of interest can be used. For example, signals collected in a period close to the event episode would likely give a reasonable estimate of the EMI frequency at the event episode.

The basis function filter and method are best suited for applications involving post-processing of recorded waveforms, although a real-time implementation can be done if sufficient processing power is available and if delays in the filter output can be tolerated.

Estimation of the EMI Frequencies

Often, the EMI frequency (e.g., the power line frequency) is non-stationary (over time). For better filter performance, the EMI frequency is repeatedly estimated (by examining the power spectrum of contiguous regions of the observed input, y). The choice for the duration of these regions will depend on the sample rate, expected variations from EMI frequency (e.g., nominal line frequency) at a given recording site, and the degree of EMI filtering desired. The duration is selected (e.g., 5, 10, 30, 60 seconds, etc.) in view of the assumption that the EMI frequencies will be reasonably stationary over that duration. The EMI frequency (or frequencies) is determined from the spectral analysis. Similarly, the EMI frequencies can be determined from the appropriate analysis of signals suspected of having square-wave-type EMI.

Figure 4:
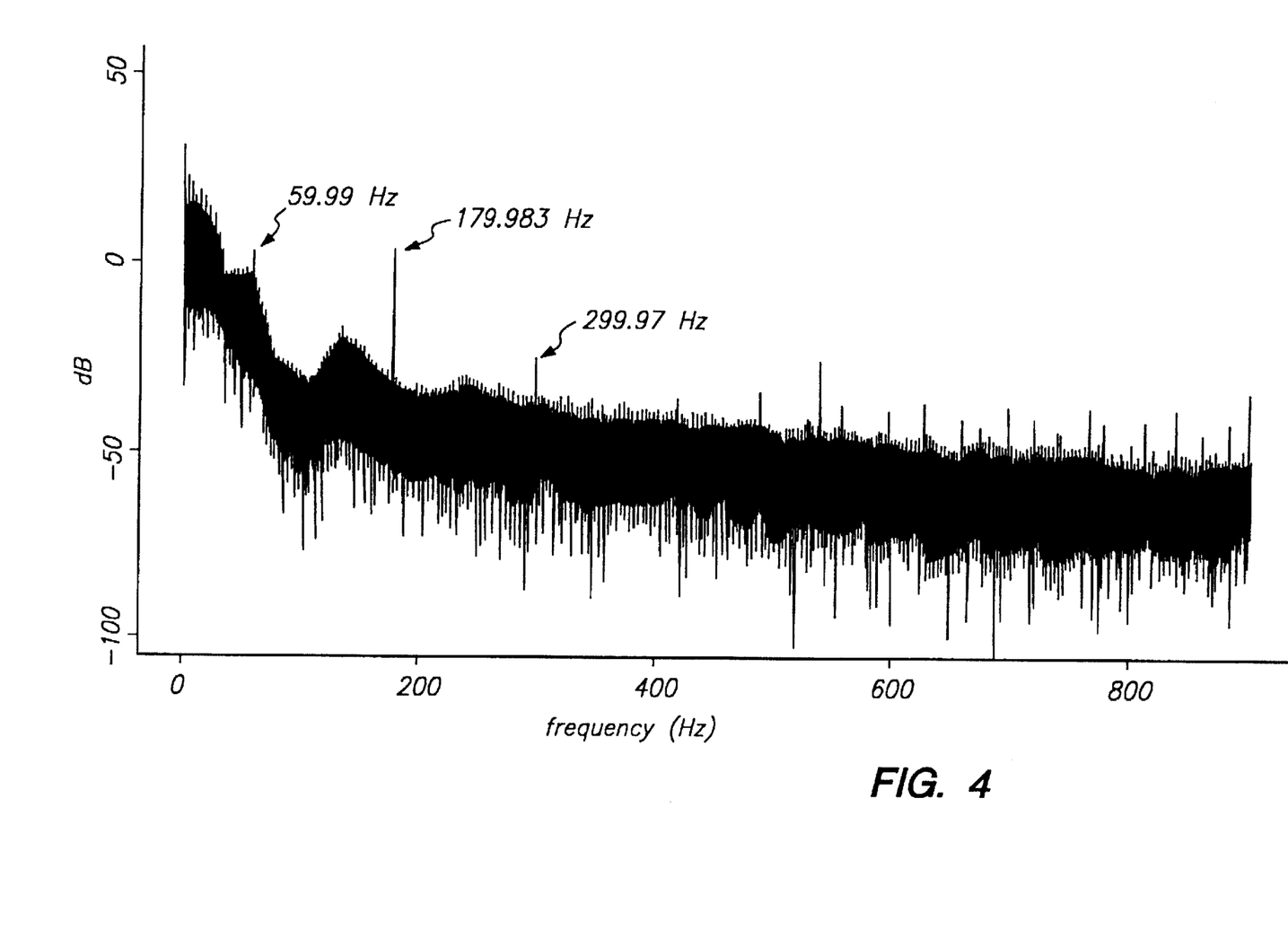
FIG. 4 shows a typical power spectrum of ECG signals collected over a time period.

For example, to find the EMI frequencies of line frequencies, a search is made for peaks in the power spectrum in the vicinity of the nominal power line frequency (e.g., 60 Hz) and its harmonics (e.g., 3rd; 180 Hz; 5th; 300 Hz). An example of a spectrum computed from 60 seconds of ECG is shown in FIG. 4. Usually only a few of the harmonics (e.g., the odd harmonics of base line frequency 60 Hz of EMI in ECG) are dominant. These may contain more energy than the power base line frequency itself.

As an illustration, sinusoidal EMI at the frequencies of these identified peaks are to be eliminated by the present filter method. We refer to these selected frequencies as $f_i$, wherein i=1, 2, . . . , m.

In cases where the EMI frequencies and the signals' spectral content overlap, some of the EMI peaks (e.g., at 60 Hz) may not be discernable in the power spectrum. In these cases, a search can be made for the frequency of the most dominant EMI harmonic (e.g., at 180 Hz). Searching methods known in the art can be used. Once the dominant harmonic's peak is found (e.g., the 3rd harmonic at 180.3 Hz), by appropriate scaling one can determine the mains (or fundamental) frequency (e.g., divide by 3 to get 60.1 Hz) and the other harmonics (e.g., for the 5th harmonic multiply by 5/3 to get 300.5 Hz).

EMI Frequency Power and Phase Estimation

The EMI is then estimated by matching the basis function (s) with the signal data. For example, the "sinusoidal trends" of the EMI are obtained by a curve-fitting method (e.g., a regression method), which estimates the amplitude and phase at each EMI frequency). First, an event epoch (during which signals of the event of interest are present) having input $y_e$ is identified in the observed input y (which is in voltage units). Next, a quiet epoch having input $y_q$ is identified which precedes and is adjacent to the event epoch. This quiet epoch contains mostly EMI. A variety of methods (including standard methods) for identifying events can be used. For example, in ECG signals, the QRS complex can be identified by its large amplitude. The P and the T waves can then be identified based on their relation to the QRS complex. The beginning and the end of the event epoch can be determined based on the inflection of the curve before the P wave and after the T wave.

Figure 5:
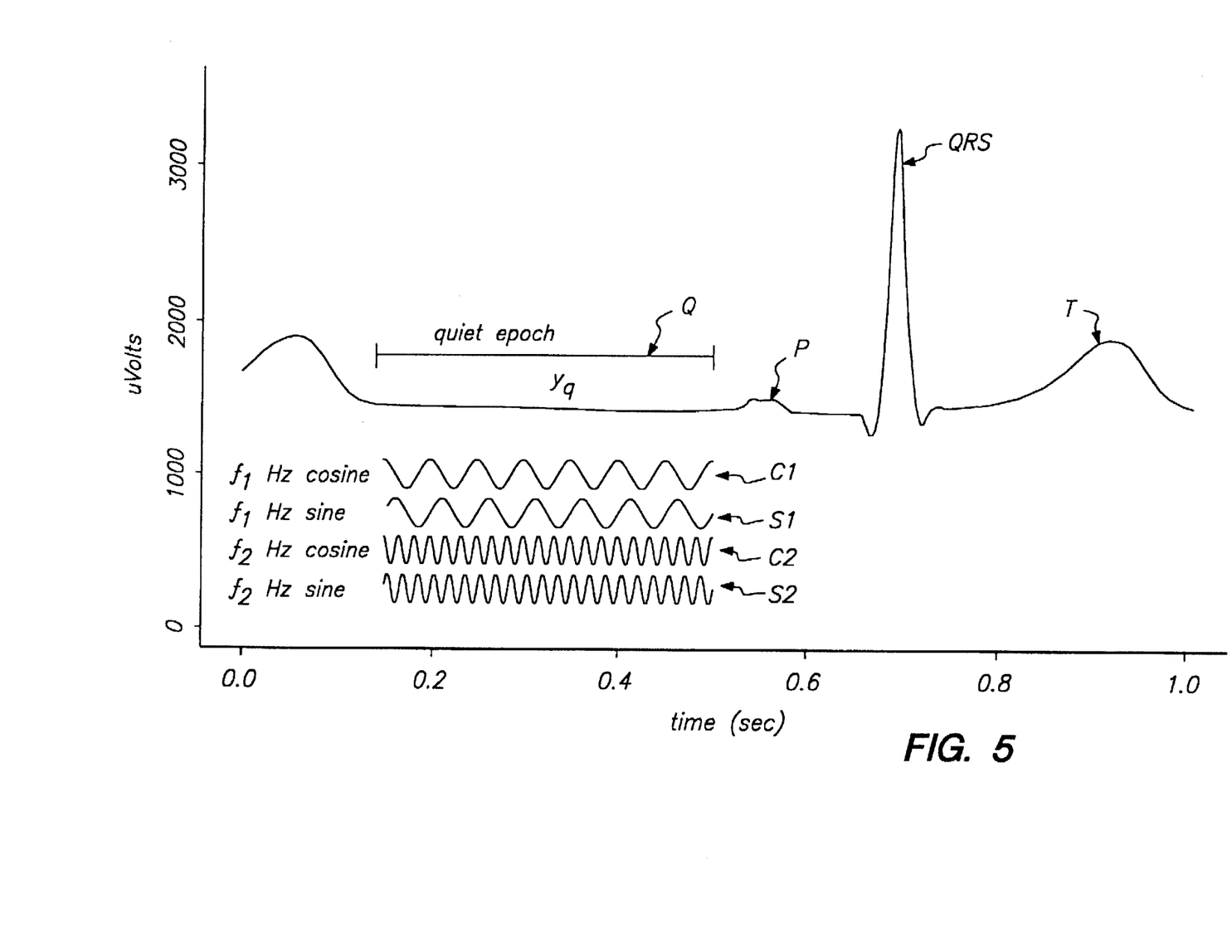
FIG. 5 shows an event episode of ECG and the basis functions used for matching the interference during the quiet epoch in the event episode.

Basis functions (e.g., sinusoidal ones) are then generated to span the quiet epoch. For line EMI, for each of the m EMI frequencies identified in the above procedure (via spectral analysis), a cosine wave and a sine wave are created having the same sample rate (for digitizing the signals) as the signal and the duration of the quiet epoch. (See FIG. 5.) Having both a cosine wave and sine wave at each frequency allows the method to match the phase of the EMI, since a linear combination of the two can be used to create a sinusoid of arbitrary phase. (For illustration purposes, the cosine wave C1 and sine wave S1 of a first dominant frequency, as well as the cosine wave C2 and sine wave S2 of a second dominant frequency are shown in FIG. 5.) It is noted that having knowledge of the nature of the EMI will be beneficial in identifying the basis functions applicable. For line EMI, the basis functions are sine waves and cosine waves. For rectangular EMI waves, basis functions that generate rectangular functions can be use.

In the line EMI example, the sample values for each basis function are placed in adjacent columns of an $n_q$ by 2m matrix "Q," where $n_q$ is the number of sample points in the quiet epoch, and 2m is the number of basis functions (and is twice the number of EMI frequencies to be filtered because both a sine wave and a cosine wave are included). The value of m is selected to include the more dominant EMI frequencies. For example, in ECG filtration, there are three EMI frequencies that are predominant (60 Hz, 180 Hz, and 300 Hz). It is contemplated that in other signal measurement cases, other predominant EMI frequencies can be present. For example, in cases where signal measurement is done in the vicinity of an oscillator (e.g., in communication equipment, television sets, etc.), the oscillator can generate EMI that interferes with the signals of interest.

The $n_q$ digital samples of the quiet epoch comprise the "observation" vector "$y_q$." To estimate line EMI, the linear combination of the basis functions of an EMI angular frequency $\omega$ has the form A cosine $\omega t$+B sin $\omega t$ where t is time and A and B are amplitudes.

The 2m coefficients (or "weights") in the solution estimate vector, "x," are then computed to solve the following equation best:

$$Qx=y_q \qquad \text{Eq 1.}$$

A number of regression methods can be employed to solve for x in this equation. One frequently used method minimizes the squared error between the interference estimate $\hat{i}_q$ and the observations in the quiet epoch:

$$\epsilon^2=(\hat{i}_q-y_q)^T(\hat{i}_q-y_q) \qquad \text{Eq 2.}$$

The formal solution is given in terms of the pseudoinverse, $Q^{-1}$:

$$\hat{x}=Q^{-1}y_q=(Q^TQ)^{-1}Q^Ty_q \qquad \text{Eq 3.}$$

The 2m basis functions are then multiplied by the solution coefficients and summed together to form the estimate of the interference $\hat{i}_q$ in the quiet epoch:

$$\hat{i}_q=Q\hat{x} \qquad \text{Eq 4.}$$

Removal of the EMI from the Collected Signals to Recover the Event Signals

The "quiet-epoch" EMI estimate (e.g., the sinusoidal trend) created from the quiet epoch is extended across the adjacent event epoch to create an EMI estimate of the event epoch. This "event-epoch" EMI estimate is then subtracted from the signals of the event epoch, effectively filtering the EMI signals to recover the event signals.

Figure 6:
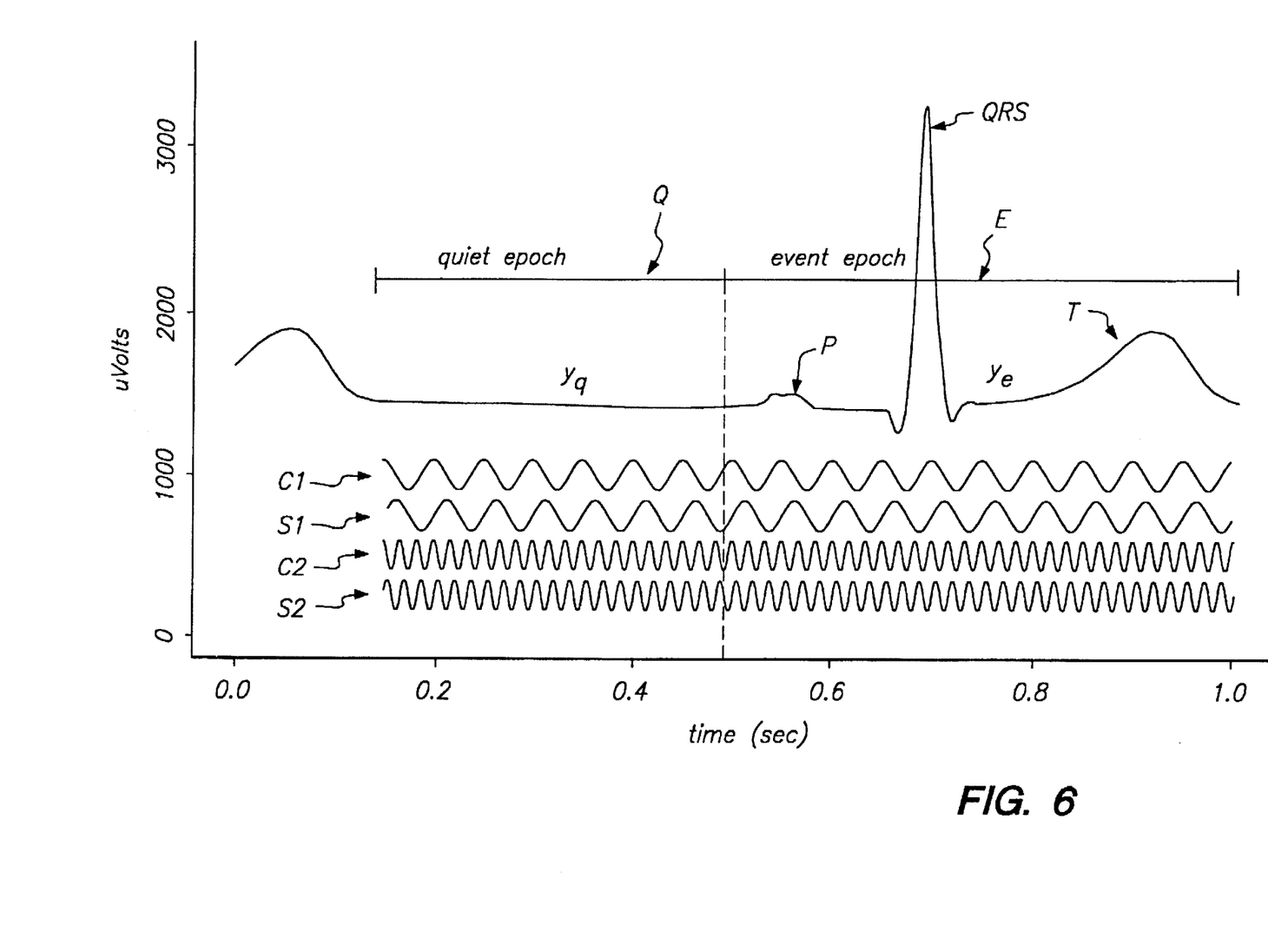
FIG. 6 shows the event episode of FIG. 3 and the basis functions used for matching the interference during the quiet epoch being extended to span the event epoch.

The EMI estimate vector $\hat{i}_q$ created in the above typically cannot be used directly as an estimate of the EMI during the event epoch, since its basis functions (e.g., cosine trends for sinusoidal EMI) will likely not be in phase with those of the EMI during the event epoch. Thus, to maintain the phase relationship between the EMI fitted in the quiet epoch and the EMI estimate for the event epoch, the basis functions are extended from their original starting points to span both the quiet and event epochs, as shown in FIG. 6.

For sinusoidal trends functions using the above regression method, a new matrix Q' is therefore created to contain $n_e$ additional rows which extend the sinusoids in the columns of Q, where $n_e$ is the number of points required to span the event epoch. This new matrix can be viewed as having two portions: the upper portion Q containing the basis functions spanning the quiet epoch, and the lower portion E containing the continuation of the basis functions, which span the event epoch. Thus Q' has the form $$Q'=\begin{bmatrix} Q \\ E \end{bmatrix}. \qquad \text{Eq 5}$$

The interference estimate $\hat{i}_e$ for the event epoch is then found by multiplying the portion of the basis functions E which had been extended to span the event epoch by $\hat{x}$, the coefficients found in the above $$\hat{i}_e=E\hat{x} \qquad \text{Eq 6.}$$

Finally, the filtered event signal $S_e$ is found by point-by-point subtraction of the EMI estimate $\hat{i}$ from the original observed event waveform $y_e$:

$$S_e=y_e-\hat{i}_e \qquad \text{Eq 7.}$$

where the subtraction is performed only over the event epoch.

Repetition of the Method for Each Event

The EMI estimation and removal by subtraction are alternately repeated for each event epoch within the region of the waveform which has been used to determine the EMI frequencies from the power spectrum. When the end of this region is reached, the entire process is repeated for another region of data.

The effectiveness of the removal of the EMI from the collected signals during the event episode depends on the stationarily of the EMI throughout the quiet and event epochs. EMI amplitude, phase, or frequency changes during these intervals will cause degradation of filter performance. Such occurrences are preferably identified so that the event epoch can be deleted from subsequent analysis. This can be achieved by comparing the EMI estimate determined from the preceding quiet epoch to an EMI estimate computed from the quiet epoch which follows the event epoch being filtered. The degree of match between these two estimates is an indication of the degree of stationarily of the EMI.

Figure 7:
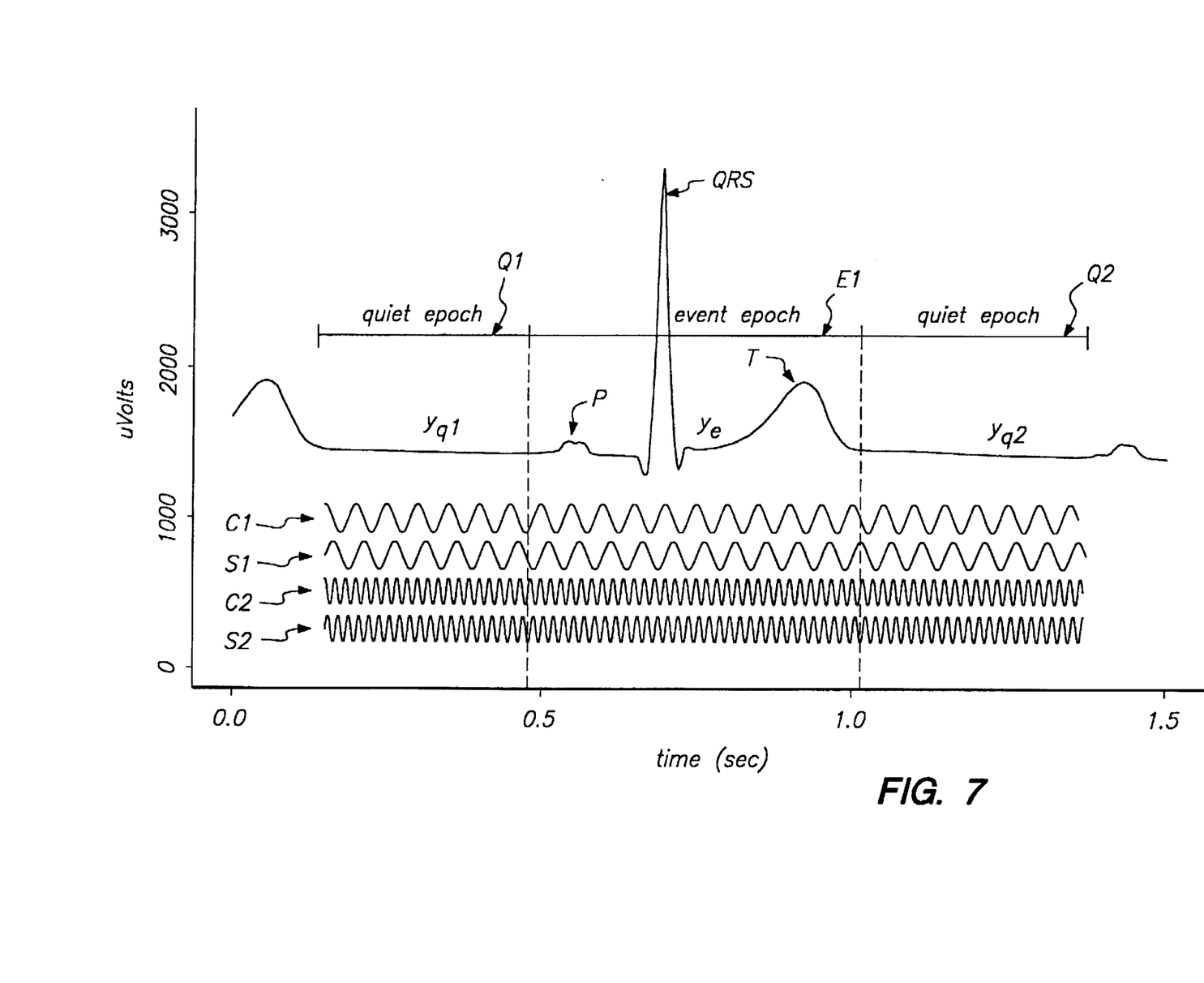
FIG. 7 shows portions of event episodes including quiet epochs adjoining an event epoch and the quiet epochs being used to estimate the EMI of the event epoch to result in weighted basis functions.

Although only one quiet epoch preceding each event epoch is described to determine the EMI estimate for each event epoch, the filter method can be made more robust by using additional quiet epochs in each estimate determination. For example, the two quiet epochs (e.g., Q1 and Q2) flanking each event epoch (e.g., E1) can be used, as shown in FIG. 7.

In this case a matrix whose columns are the basis functions having sufficient length to span the first (preceding) quiet epoch, the event epoch, and finally the second (succeeding) quiet epoch is created. This matrix has three respective components:

$$\begin{bmatrix} Q_1 \\ E \\ Q_2 \end{bmatrix} \quad \text{Eq 8}$$

where E is the portion of the basis functions that spans the event epoch. The regression equation to be solved is then given by:

$$\begin{bmatrix} Q_1 \\ Q_2 \end{bmatrix} x = \begin{bmatrix} y_{q1} \\ y_{q2} \end{bmatrix} \quad \text{Eq 9}$$

where $y_{q1}$ and $y_{q2}$ are the portions of the input waveform in the two quiet epochs and are concatenated to form the observation vector. The rows corresponding to the event epoch in both the basis functions and the observation vector are deleted. Any regression method can then be used to solve this equation for $\hat{\imath}$ with no ill effects due to the deletion of these elements. The interference estimate over the surrounded event epoch is then given by:

$$\hat{\imath}_e = E\hat{x} \quad \text{Eq 10.}$$

Depending on the nature of the signals (e.g., duration of the quiet/event epochs), any number of quiet epochs surrounding each event epoch can be used in a similar manner. For example, the two quiet epochs preceding and the two following an event epoch can be used.

Once digitized signals are obtained, the analysis of the spectrum, the estimation of EMI, and the subtraction of the estimated EMI from the digitized signals (data) can be done in any electronic mechanisms that are under the direction of a computer program or electronic equivalents that perform such operations. For example, an electronic computer can contain a computer program that receives an input of the digitized data and performs the spectral analysis, estimation of EMI, and subtraction of the estimated EMI from the digitized signals in a fashion consistent with the above-described mathematical description or similar methods. A person skilled in the art will be able to write such computer programs based on the above-described method of filtering EMI. Also, such computer programs may be stored in program storage media. For example, such a computer program may be stored in the memory of a computer or stored in an external program memory medium such as a hard disk, floppy disk, magnetic tape, compact disk, and the like. Such a program can be loaded (or read) into a computer (or a similar device) to enable the computer to filter EMI from digitized signals.

Other Embodiments

In certain applications it may be difficult to identify quiet epochs in which only EMI, but no event signal content, is present. However, there may be brief portions of the waveform in which event signal is present, but nevertheless can be separated from the EMI using traditional filtering methods. For example, the beginning and/or the end of each event (e.g., a PQRST ECG wave) may contain signal content at frequencies substantially below the lowest EMI frequency. A traditional highpass filter allows this portion of the signal to be suppressed. A digital finite-impulse-response (FIR) highpass filter with a slow rolloff can thus be used to filter the observed waveform to produce the quiet epochs. This filter will result in smaller coefficients for these EMI frequency estimates and produces an EMI estimate over the event epoch which underestimates the power at these frequencies.

A solution is to scale up these coefficients by the amount of attenuation the highpass filter produces at the corresponding frequency. These scaling factors can be computed a priori, since they remain constant. Highpass filtering the quiet epochs can also remove low-frequency interference (e.g., drift or baseline wander)

In applications where the EMI is expected to remain relatively stationary over longer periods and in which epoch boundary determination errors and/or other interference are expected to be present, another way to add robustness is to constrain the epoch-to-epoch deviations of the estimated EMI coefficients. Constraining the mount of allowed deviation will decrease sensitivity to transient interference from non-EMI sources. To do this, for example, the sum of the squares of the cosine and sine coefficients of the estimate at each frequency can be constrained in the amount that it can vary. (The power at each frequency, not just each individual coefficient, must be constrained, since the cosine and sine coefficients for each frequency vary from epoch to epoch to handle variations in the EMI phase). Once the constrained power is determined, both corresponding coefficients are scaled in proportion to the ratio of the power of the original estimate to that of the constrained value.

The method employed to constrain the coefficient deviations will depend on the expected measurement errors, interference, and typical EMI variations. Examples of constraining methods are: 1) constraining the power estimate at a given frequency to vary by no more than 10% from that of the preceding epoch, and 2) low-pass filtering the power estimates with a simple filter.

To produce a continuously filtered output stream one only needs to subtract the EMI estimate $\hat{\imath}_q$ determined using the quiet epoch from the quiet epoch's samples. A number of surrounding quiet epochs could also be used in addition to the "central" quiet epoch itself to estimate the EMI. In such an implementation, filtering of a quiet epoch would alternate with filtering of an event epoch. The two types of epochs are processed similarly, except the central quiet epoch is included, whereas the central event epoch is deleted from the regression equations.

Figure 8:
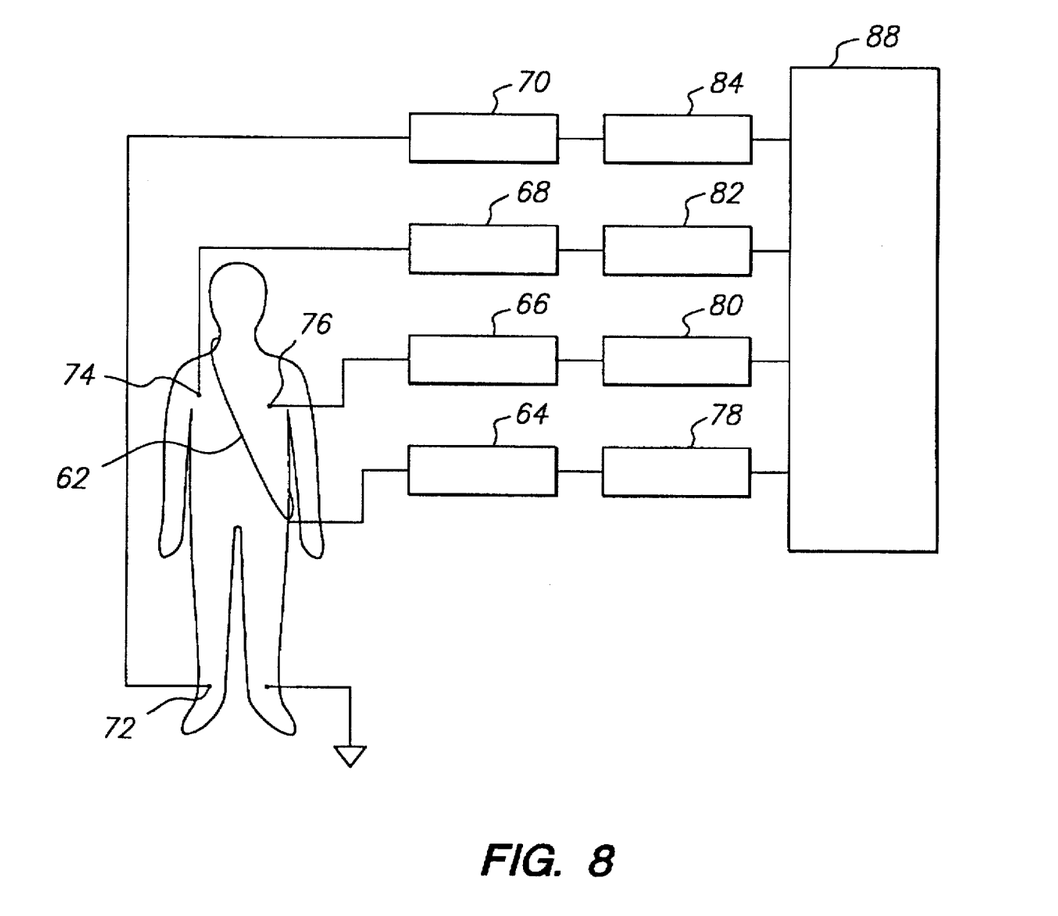
FIG. 8 illustrates the use of an EMI sensor for collecting EMI signals at a location different from that of a sensor that collects event signals.

The sinusoidal trend filter exploits the time diversity of the signal. Spatial diversity can also be employed to detect event epochs in which the basis function filter may be insufficient due to sudden brief bursts in the EMI isolated to the event epoch. Simultaneous recordings of signals from an EMI-detecting sensor (isolated from primary signals), such as an inductive loop 62 across the shoulder and chest of a patient in FIG. 8, can be used to verify the stationarily or non-stationarily of the EMI throughout both the quiet and event epochs at each iteration of the method. This can be done by simultaneously implementing the filter on these channels, in parallel to the signal (i.e., by using the same epoch boundaries). The EMI residuals over the event epoch can be examined; they should be small (ideally zero) if the EMI is stationary and has been estimated accurately. Large residuals would flag an event epoch as improperly filtered, i.e., as a transitory failure of the method, requiring the episode be deleted in subsequent data analysis. Such flagging can be done by a computer. The embodiment of FIG. 8 can have the amplifiers 64, 66, 68, 70 to amplify signals from the loop 62 and ECG electrodes 72, 74, 76. The signals can then pass through A/D converters 78, 80, 82, 84 and be processed by an electronic computer which performs filtering using the basis function method of the present invention.

Robust Regression Estimation Methods

One way to reduce the basis function filter's sensitivity to outliers (i.e., data points in the quiet epoch which are not parts of stationary sinusoids) is to use a robust regression method. Least one-norm (least sum of the absolute values of the residuals) (Bloomfield et al., *Least Absolute Deviations: Theory, Applications, and Algorithms*, Boston, Birkauser, 1983) and least-trimmed squares (least sum of the smallest half of the residuals) (Rousseeuw, A. L., *Robust Regression and Outlier Detection*, Wiley, N.Y., 1987) are examples of such robust methods.

The choice of regression method, nevertheless, is application-dependent, affected by the nature of the overall interference present in the waveform. For example, if the only other interference in addition to the EMI has a Gaussian distribution (e.g., muscle tremor in physiological recordings), the least-squared error method (as described above in the equations) will actually provide the best results. In addition, a least-squared error regression is straightforward and efficient to implement compared to the algorithms required for some of the robust methods.

It is understood that modifications can be made by a person skilled in the art without departing from the scope and spirit of the claims. For example, computer programs can be stored in a program storage medium to be loaded into a computer or a similar device for filtering out EMI based on the various embodiments described.

What is claimed is:

1. Apparatus for filtering signals of a series of generally periodic events each having an event episode including an event epoch and a quiet epoch, the apparatus comprising:

(a) means for generating electrical digitized signals of the event episodes;

(b) memory connected for receiving and storing the digitized signals of the event episodes;

(c) event detector connected to determine the event epoch and the quiet epochs of the event episodes for the events in the digitized signals;

(d) spectrum analyzer connected to analyze power spectra of the digitized signals, each spectrum being based on at least one event episode of the events at a time;

(e) estimator connected to estimate electromagnetic interference (EMI) by comparing the digitized signals of a quiet epoch of the at least one event episode with basis function at one or more frequencies identified in a spectrum in the spectral analysis by the spectrum analyzer to obtain an EMI estimate; such that the estimator by said spectra can obtain EMI estimates adapted to a shift in frequency phase or amplitude in the EMI for EMI that varies with time; and (f) subtractor connected to subtract from the digitized signals of the event epochs the EMI estimates derived from corresponding spectra such that the resulting signals for the event epochs have reduced EMI.

2. The apparatus according to claim 1 wherein the estimator is adapted to combine a sine wave and a cosine wave of an EMI frequency determined from the spectral analysis to fit data of the signals of the quiet epoch to generate the EMI estimate.

3. The apparatus according to claim 2 wherein only one sine wave and only one cosine wave of the EMI frequency are combined to fit data of the quiet epoch at the EMI frequency, said sine wave and said cosine wave can have different amplitudes, each of said amplitudes being selected such that the combination of said sine wave and said cosine wave generates the EMI estimate at the EMI frequency.

4. The apparatus according to claim 2 wherein the estimator is adapted to generate an EMI estimate having a fundamental frequency and one or more of its harmonic frequencies.

5. The apparatus according to claim 2 wherein the estimator is adapted to estimate the EMI by combining a sine wave and a cosine wave of an EMI frequency determined from combined data including data of signals from at least two quiet epochs.

6. The apparatus according to claim 1 wherein the memory, event detector, estimator, and subtractor are part of an electronic computer.

7. The apparatus according to claim 1 wherein the means for generating electrical digitized signals comprises an analog-to-digital converter connectable to a sensor for collecting the signals of the event episodes from a signal source.

8. The apparatus according to claim 1 wherein the means for generating electrical digitized signals comprises a sensor adapted to collect signals of the event episodes from a signal source.

9. The apparatus according to claim 8 wherein the sensor comprises electrocardiogram (ECG) electrodes for attaching to a patient.

10. The apparatus according to claim 8 further comprising an EMI-signal-collector to be positioned on the patient at a location different from that of the sensor such that the EMI-signal-collector's EMI signals during the quiet epoch of an event can be compared with its EMI signals collected during the event epoch of the event so that event epochs during which unusual EMI signals occur can be discarded.

11. The apparatus according to claim 1 further comprising a high-pass filter connected to suppress non-EMI signals from the quiet epoch in an event before the estimator and wherein the estimator scales up the estimate to compensate for attenuation of the EMI in the quiet-epoch signals by the high-pass filter.

12. The apparatus according to claim 1 wherein the estimator comprises a robust means for estimating EMI such that the effect of outlier signals is reduced.

13. The apparatus according to claim 1 wherein the estimator compares blocks of data of signals of the quiet epochs to blocks of data of basis functions for estimating EMI for the event episodes.

14. The apparatus according to claim 1 wherein the estimator by means of the spectra can adapt to a shift in EMI frequency.

15. Apparatus for filtering electrocardiogram (ECG) signals of a series of heart beats each having a cardiac event episode including an event epoch suspected of containing signals of interest and a quiet epoch suspected to be free of said signals of interest, the apparatus comprising:

(a) detector for detecting analog ECG signals from a patient;

(b) analog-to-digital converter connected for converting the analog ECG signals to digitized signals; and (c) computer connected for receiving and storing the digitized signals of the event episode, for determining the event epochs and the quiet epochs of the event episodes in the digitized signals of the series of the art beats, for analyzing power spectra of the digitized signals, each spectrum being based on the signals of at least one event episode, for estimating electromagnetic interference (EMI) to determine an EMI estimate for each of the event epochs based on the frequencies obtained in the spectrum corresponding to said each of the event epochs such that the estimator by means of the spectra can adapt to a shift in frequency in the EMI for EMI that varies in frequency with time; and for subtracting the EMI estimates from the digitized signals of the corresponding event epoch such that the resulting signals for the event epochs have reduced EMI, said estimating for each event epoch comprises filtering the signals of a quiet epoch of the at least one event episode with a high-pass filter to supress non-EMI signals in the signals of the quiet epoch, combining a sine wave and a cosine wave of an EMI frequency determined from the spectral analysis to approximate data of the signals of the quiet epoch after non-EMI-signal-suppression such that a block of data of the signals of the quiet epoch is compared to a block of data of sine and cosine waves to generate a first EMI estimate, and scaling up the first EMI estimate to compensate for attenuation of EMI in the signals of the quiet epoch by the high-pass filter to arrive at the EMI estimate for the subtraction.

16. A method for filtering signals of a series of generally periodic events each having an event episode including an event epoch and a quiet epoch, the method comprising:

(a) detecting signals of the event epochs and quiet epochs of the generally periodic events;

(b) analyzing power spectra, each spectrum being based on signals of at least one of the event episodes;

(c) estimating electromagnetic interference (EMI) of the event epochs, said estimating from each event including matching signals of at least one quiet epoch of the at least one of the event episodes to basis functions of one or more frequencies identified in a spectrum corresponding to said at least one of the event episodes, such that the estimating step can adapt to a shift in frequency, phase, or amplitude in the EMI for EMI that varies with time; and (d) subtracting the corresponding estimated EMI from the signals of the event epoch such that the resulting signals are signals of the event epochs with reduced EMI.

17. The method according to claim 16 wherein the signals are digitized signals and wherein estimating EMI for an event epoch comprises combining a sine wave and a cosine wave of an EMI frequency determined from the spectral analysis to fit data of the signals of the quiet epoch corresponding to said event epoch.

18. The method according to claim 17 wherein only one sine wave and only one cosine wave of the EMI frequency are combined to fit data of the quiet epoch at the EMI frequency, said sine wave and said cosine wave can have different amplitudes, each of said amplitudes being selected such that the combination of said sine wave and said cosine wave generates the estimated EMI at the EMI frequency.

19. The method according to claim 17 wherein estimating EMI generates an EMI estimate having a fundamental frequency and one or more harmonic frequencies of said fundamental frequency.

20. The method according to claim 17 wherein estimating EMI comprises combining a sine wave and a cosine wave of an EMI frequency which is determined from combined data including data of signals of at least two quiet epochs.

21. The method according to claim 16 further comprising converting analog signals to digital signals before estimating EMI.

22. The method according to claim 16 further comprising collecting signals from a signal source.

23. The method according to claim 16 further comprising collecting electrocardiogram (ECG) signals of a patient for filtering of EMI.

24. The method according to claim 16 further comprising collecting signals of the event episodes for filtering of EMI and collecting EMI signals at a location different from where the signals of the event episodes are collected so that EMI signals collected thereby from said different location during a quiet epoch can be compared with EMI signals collected during the corresponding event epoch so that event epochs during which unusual EMI signals occur can be discarded.

25. A program storage medium readably by a computer, tangibly embodying a program of instruction including code means executable by the computer to digitally filter signals of a series of events each having an event episode including an event epoch and a quiet epoch, the program storage medium comprising:

a memory device having code means including, (a) code means for detecting the event epochs and the quiet epochs for the series prevents;

(b) code means for analyzing power spectra of digitized signals, each spectrum being based on at least one event episodes of the events;

(c) code means for estimating electromagnetic interference (EMI) of the event epoch, for each event epoch said code means for estimating matches signals of a quiet epoch of the at least one event episode of a corresponding spectrum to a combination of a sine wave and a cosine wave at an EMI frequency determined from the spectrum to fit data of the signals of the quiet epoch to arrive at a first estimate, said estimating code means including a high-pass-filter for suppressing non-EMI signals from the signals of the quiet epoch and a means to scale up the first estimate obtained by said matching to compensate for attenuation of EMI the signals of the quiet epoch by the high-pass-filter to arrive at the EMI estimate, such that said code means for estimating can adapt to a shift in frequency in the EMI for EMI that varies in frequency with time; and (d) code means for subtracting the corresponding estimated EMI from the signals of the event epochs such that the resulting signals are signals of the event epochs with reduced EMI.

* * * * *